United States Patent
Nakazono et al.

(10) Patent No.: US 11,225,680 B2
(45) Date of Patent: Jan. 18, 2022

(54) PREDICTION-RULE GENERATING SYSTEM, PREDICTION SYSTEM, PREDICTION-RULE GENERATING METHOD, AND PREDICTION METHOD

(71) Applicant: Sumitomo Chemical Company, Limited, Tokyo (JP)

(72) Inventors: Akiko Nakazono, Ibaraki (JP); Fumiyoshi Okazaki, Mie (JP); Hiroyuki Asako, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 368 days.

(21) Appl. No.: 15/562,622

(22) PCT Filed: Mar. 30, 2016

(86) PCT No.: PCT/JP2016/060516
§ 371 (c)(1),
(2) Date: Sep. 28, 2017

(87) PCT Pub. No.: WO2016/159154
PCT Pub. Date: Oct. 6, 2016

(65) Prior Publication Data
US 2018/0105858 A1    Apr. 19, 2018

(30) Foreign Application Priority Data

Apr. 3, 2015    (JP) .............................. JP2015-076945

(51) Int. Cl.
| | |
|---|---|
| G01N 33/48 | (2006.01) |
| C12Q 1/06 | (2006.01) |
| C02F 3/12 | (2006.01) |
| G01N 33/18 | (2006.01) |
| G06G 7/58 | (2006.01) |
| G06F 17/18 | (2006.01) |

(52) U.S. Cl.
CPC ............... *C12Q 1/06* (2013.01); *C02F 3/12* (2013.01); *G01N 33/18* (2013.01); *G01N 33/1866* (2013.01); *C02F 2209/003* (2013.01); *C02F 2209/36* (2013.01); *G06F 17/18* (2013.01); *Y02W 10/10* (2015.05)

(58) Field of Classification Search
None
See application file for complete search history.

(56) References Cited

U.S. PATENT DOCUMENTS

2011/0100903 A1    5/2011   Igarashi et al.

FOREIGN PATENT DOCUMENTS

| | | |
|---|---|---|
| CN | 101825622 A | 9/2010 |
| CN | 102807301 A | 12/2012 |
| CN | 103793604 A | 5/2014 |
| CN | 103809436 A | 5/2014 |
| EP | 2181966 A4 | 2/2014 |
| JP | 2004-008176 A | 1/2004 |
| JP | 2006-326522 A | 12/2006 |
| JP | 2007-229550 A | 9/2007 |
| JP | 2007-263723 A | 10/2007 |
| JP | 2008-142704 A | 6/2008 |
| JP | 5022610 B2 | 9/2012 |
| JP | 5049748 B2 | 10/2012 |
| JP | 2014-121692 A | 7/2014 |
| WO | 2010/004938 A1 | 1/2010 |

OTHER PUBLICATIONS

International Search Report issued in corresponding International Patent Application No. PCT/JP2016/060516 dated May 24, 2016.
International Preliminary Report on Patentability issued in corresponding International Patent Application No. PCT/JP2016/060516 dated Oct. 12, 2017.
Office Action issued in counterpart Indian Patent Application No. 201747037684 dated Jan. 4, 2021.
Zhao Xi, "The Mechanism and Practice of Aerobic Microorganism in wastewater Purification", Chinese Doctoral Dissertations & Masters Theses Full-text Database(Master) Engineering Science and Technology I, No. 5 B027-164, May 15, 2007.
Office Action issued in corresponding Chinese Patent Application No. 201680019682.8 dated Mar. 20, 2020.
Office Action issued in counterpart Taiwanese Patent Application No. 105110649 dated Dec. 10, 2019.

*Primary Examiner* — Eric S Dejong
(74) *Attorney, Agent, or Firm* — Morgan, Lewis & Bockius LLP

(57) ABSTRACT

A computer of a prediction-rule generating system includes an input unit configured to input time series data of an abundance proportion of microorganisms or nucleotide sequences included in activated sludge in which a water treatment is performed and water quality information indicating water quality after a water treatment associated with data at each time constituting the time series data, a principal component analyzing unit configured to perform principal component analysis on the input time series data and calculate principal component scores of data at each time constituting time series data, and a prediction rule generating unit configured to generate a prediction rule for predicting water quality after a water treatment from an abundance proportion of microorganisms or nucleotide sequences on the basis of the calculated principal component scores and the input water quality information indicating water quality after a water treatment.

20 Claims, 5 Drawing Sheets
Specification includes a Sequence Listing.

PREDICTION-RULE GENERATING SYSTEM, PREDICTION SYSTEM, PREDICTION-RULE GENERATING METHOD, AND PREDICTION METHOD

SEQUENCE LISTING SUBMISSION VIA EFS-WEB

A computer readable text file, entitled "SequenceListing.txt," created on or about Sep. 27, 2017 with a file size of about 2 kb contains the sequence listing for this application and is hereby incorporated by reference in its entirety.

TECHNICAL FIELD

The present invention relates to a prediction-rule generating system and a prediction-rule generating method through which a prediction rule for predicting water quality after a water treatment is generated, and a prediction system and a prediction method related thereto.

BACKGROUND ART

It is desirable that wastewater in heavy and chemical industries such as chemical and steel industries which has a sufficiently reduced influence on humans and environmental organisms be discharged to the natural environment. As a wastewater treatment therefor, a biological treatment in which activated sludge which is a complex microbial system is used is performed. In general, in order to appropriately perform a wastewater treatment, water quality of wastewater after the treatment is monitored. Specifically, water quality is monitored by obtaining water quality measurement data such as biochemical oxygen demand (BOD), chemical oxygen demand (COD), total organic carbon (TOC), and total nitrogen (TN) of wastewater after the treatment. In order to obtain a measurement result of BOD, which is an important management index in a biological treatment, generally a time of about 5 days is taken. Therefore, BOD on the same day may be estimated based on other water quality data and operating parameters of a biological reaction tank such as a temperature, a pH, and a dissolved oxygen concentration (DO). In addition, predicting of future values of water quality data such as BOD, COD, TOC, and TN from the current state of wastewater is important for management, and biochemical oxygen demand (BOD) and the like are predicted on the basis of time series data of water quality and time series data of operating parameters of a biological reaction tank (refer to Patent Literature 1 and 2).

CITATION LIST

Patent Literature

[Patent Literature 1] Japanese Unexamined Patent Publication No. 2007-229550
[Patent Literature 2] Japanese Unexamined Patent Publication No. 2007-263723

SUMMARY OF INVENTION

Technical Problem

However, when prediction is performed using time series data of water quality and operating parameters of a biological reaction tank described above, states of microbial flora in activated sludge are not considered, and prediction is not performed with sufficient accuracy in some cases. It is particularly difficult to perform prediction in situations in which various wastewaters are treated. Therefore, it is necessary to improve prediction accuracy when the state of treated water is predicted.

The present invention has been made in view of the above circumstances, and provides a prediction-rule generating system and a prediction-rule generating method through which it is possible to generate a prediction rule by which water quality after a water treatment is accurately and reliably predicted, and a prediction system and a prediction method related thereto.

Solution to Problem

In order to achieve the above object, a prediction-rule generating system according to an embodiment of the present invention includes input means configured to input time series data of an abundance proportion of each of a plurality of microorganisms included in activated sludge in which a water treatment is performed or an abundance proportion of each of a plurality of nucleotide sequences included in the activated sludge (hereinafter referred to as "time series data of microorganism information" in some cases) and water quality information indicating water quality after a water treatment associated with data at each time constituting the time series data, principal component analyzing means configured to perform principal component analysis on the time series data input by the input means and calculate principal component scores of data at each time constituting the time series data, and prediction rule generating means configured to generate a prediction rule for predicting water quality after a water treatment from an abundance proportion of each of the plurality of microorganisms or an abundance proportion of each of the plurality of nucleotide sequences on the basis of the principal component scores of data at each time constituting time series data calculated by the principal component analyzing means and the water quality information indicating water quality after a water treatment associated with data at each time constituting the time series data input by the input means. As the water quality after a water treatment, for example, biochemical oxygen demand (BOD), chemical oxygen demand (COD), total organic carbon (TOC) and total nitrogen (TN) in treated water are exemplified.

The prediction-rule generating system according to the embodiment of the present invention generates a prediction rule on the basis of time series data of abundance proportions of microorganisms or nucleotide sequences included in activated sludge in which a water treatment is performed and water quality information indicating water quality after a water treatment associated with data at each time constituting the time series data. Therefore, it is possible to perform prediction in consideration of states of microbial flora in activated sludge, and prediction can be performed accurately compared to when prediction is performed using only time series data of water quality and operating parameters of the biological reaction tank.

In addition, in the prediction-rule generating system according to the embodiment of the present invention, principal component analysis is performed. In general, the number of types of microorganism included in activated sludge is extremely large. By performing principal component analysis on time series data of microorganism information, all information is captured without reducing an amount of information, and it is possible to express microorganism information with a small number of variables. By performing principal component analysis as in the embodiment of the present embodiment and reducing the number of variables used to generate a prediction rule, the prediction rule can be reliably generated. That is, in the prediction-rule generating system according to the embodiment of the present invention, it is possible to generate a prediction rule by which water quality after a water treatment is predicted accurately and reliably.

The principal component analyzing means may perform principal component analysis using a correlation matrix. In the principal component analysis using a variance-covariance matrix, behaviors of microorganisms of majority species are mainly reflected. On the other hand, when principal component analysis using a correlation matrix is used as in such a configuration, many variables are necessary compared to when a variance-covariance matrix is used, but it is possible to generate a prediction rule in which behaviors of microorganisms of minority species (microorganisms having a small abundance proportion) are better reflected. Behaviors of microorganisms of minority species may influence the water quality after a water treatment. Therefore, in such a configuration, it is possible to generate a prediction rule by which prediction is performed more accurately.

The prediction rule generating means may generate the prediction rule by performing machine learning in which the principal component scores of data at each time constituting time series data calculated by the principal component analyzing means are used as an input for the prediction rule and water quality information indicating water quality after a water treatment associated with data at each time constituting the time series data input by the input means is used as an output for the prediction rule. In such a configuration, it is possible to generate the prediction rule reliably.

The prediction-rule generating system may further include reading means configured to read nucleotide sequences of genes from the plurality of microorganisms included in the activated sludge, and data generating means configured to generate the time series data based on the nucleotide sequences of the genes read by the reading means and input the generated data to the input means. In such a configuration, it is possible to reliably input time series data of abundance proportions of microorganisms or nucleotide sequences, and it is possible to reliably implement an embodiment of the present invention.

A prediction system according to an embodiment of the present invention is a prediction system configured to predict water quality after a water treatment based on the prediction rule generated by the prediction-rule generating system according to the embodiment of the present invention. The prediction system includes input means configured to input data of an abundance proportion of each of a plurality of prediction target microorganisms or an abundance proportion of each of a plurality of prediction target nucleotide sequences; principal component analyzing means configured to calculate principal component scores of data of the prediction target input by the input unit on the basis of principal component analysis performed by the prediction-rule generating system; and predicting means configured to predict water quality after a water treatment from the principal component scores of data of the prediction target calculated by the principal component analyzing means based on the prediction rule generated by the prediction-rule generating system. According to the prediction system of the embodiment of the present invention, it is possible to perform prediction based on the prediction rule generated by the prediction-rule generating system.

Note that descriptions of the present invention include not only the prediction-rule generating system and the prediction system described above but also a prediction-rule generating method and a prediction method which will be described below. These are different only in category and are substantially the same invention with the same operations and effects.

That is, a prediction-rule generating method according to an embodiment of the present invention is a method of operating a prediction-rule generating system. The prediction-rule generating method includes an input step of inputting time series data of an abundance proportion of each of a plurality of microorganisms included in activated sludge in which a water treatment is performed or an abundance proportion of each of a plurality of nucleotide sequences included in the activated sludge and water quality information indicating water quality after a water treatment associated with data at each time constituting the time series data; a principal component analyzing step of performing principal component analysis on the time series data input in the input step and calculating principal component scores of data at each time constituting the time series data; and a prediction rule generating step of generating a prediction rule for predicting water quality after a water treatment from an abundance proportion of each of a plurality of microorganisms or an abundance proportion of each of a plurality of nucleotide sequences on the basis of principal component scores of data at each time constituting time series data calculated in the principal component analyzing step and water quality information indicating water quality after a water treatment associated with data at each time constituting the time series data input in the input step.

In addition, a prediction method according to an embodiment of the present invention is a method of operating a prediction system configured to predict water quality after a water treatment based on the prediction rule generated by the prediction-rule generating system according to the embodiment of the present invention. The prediction method includes an input step of inputting data of an abundance proportion of each of a plurality of prediction target microorganisms or an abundance proportion of each of a plurality of prediction target nucleotide sequences; a principal component analyzing step of calculating principal component scores of data of the prediction target input in the input step on the basis of principal component analysis performed by the prediction-rule generating system; and a predicting step of predicting water quality after a water treatment from the principal component scores of data of the prediction target calculated in the principal component analyzing step based on the prediction rule generated by the prediction-rule generating system.

Advantageous Effects of Invention

In the embodiment of the present invention, it is possible to perform prediction in consideration of states of microbial flora in activated sludge, and prediction can be performed accurately compared to when prediction is performed using only time series data of water quality and operating parameters of the biological reaction tank. In addition, in the embodiment of the present invention, by reducing the number of variables used to generate a prediction rule, the prediction rule can be reliably generated. That is, according to the embodiment of the present invention, it is possible to generate a prediction rule by which water quality after a water treatment is predicted accurately and reliably.

DESCRIPTION OF EMBODIMENTS

Figure 1:
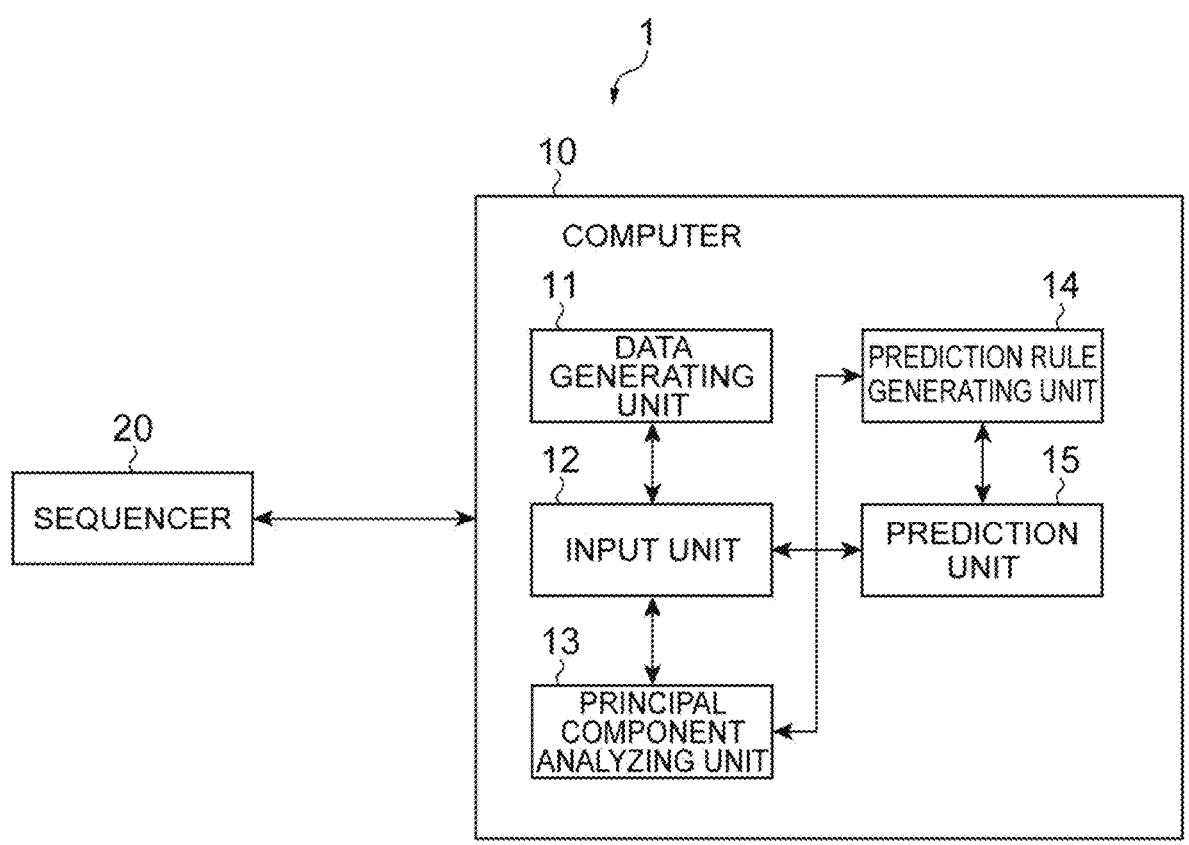
FIG. 1 is a diagram showing a configuration of a prediction-rule generating system according to an embodiment of the present invention.

A prediction-rule generating system, a prediction system, a prediction-rule generating method, and a prediction method according to embodiments of the present invention will be described below in detail with reference to the drawings. Here, in description of the drawings, the same components are denoted by the same reference numerals and redundant descriptions will be omitted.

FIG. 1 shows a prediction-rule generating system 1 according to the present embodiment. The prediction-rule generating system 1 is a system configured to generate a prediction rule for predicting water quality after a water treatment. The water treatment to be an object in the present embodiment is, for example, a treatment for reducing an influence of industrial wastewater, public sewage, dirty water, or the like, which is water that is harmful to the natural environment, on the natural environment. In addition, the water treatment is performed by a water treatment system using activated sludge including microbial flora which is clusters of a plurality of microorganisms. The number of types of microorganism included in the activated sludge is generally several thousands to several tens of thousands or more. In addition, the activated sludge is generally put into a biological reaction tank (a bio tank, an activated sludge tank), and by introducing water to be treated into the biological reaction tank, the water treatment is performed. The biological reaction tank generally includes an aerobic tank and an anaerobic tank. For example, the water treatment is continuously performed according to the operation of a factory. Here, the water treatment itself is performed conventionally.

Specifically, the prediction-rule generating system 1 generates a prediction rule for predicting whether water quality data such as BOD will exceed a preset threshold value within a preset period (for example, one week or two weeks) from a prediction time. The threshold value is, for example, a value at which it is possible to determine that water quality after a water treatment has deteriorated (the water treatment is not appropriately performed) compared to when the water treatment is appropriately performed. In addition, according to the prediction rule, prediction is performed using information based on an abundance proportion of each of a plurality of microorganisms included in activated sludge or an abundance proportion of each of a plurality of nucleotide sequences included in activated sludge as an input. That is, the prediction rule is used to predict whether deterioration including sudden deterioration of water quality data such as BOD during a preset period will occur from the above abundance proportion at a prediction time. In addition, according to the prediction rule, prediction may be performed using both an abundance proportion of each of a plurality of microorganisms and an abundance proportion of each of a plurality of nucleotide sequences as inputs. In addition, the prediction-rule generating system 1 performs prediction using the generated prediction rule. As water quality to be predicted, COD, TOC, TN, and the like can be performed similarly in addition to BOD.

As shown in FIG. 1, the prediction-rule generating system 1 includes a computer 10 and a sequencer 20. The computer 10 is a device configured to perform main functions of the prediction-rule generating system 1 and is a device configured to generate a prediction rule and perform prediction using the prediction rule. Specifically, the computer 10 includes hardware such as a central processing unit (CPU), a memory, and a communication module. When these components are operated by a program or the like, functions of the computer 10 which will be described below are executed.

The sequencer 20 is reading means configured to read (determine) nucleotide sequences of genes from a plurality of microorganisms included in activated sludge. As the sequencer 20, a so-called next generation sequencer capable of reading (analyzing) genes of a plurality of microorganisms at the same time can be used. As the sequencer 20, a sequencer in the related art, for example, a GS Junior System sequencer commercially available from Roche, a GS FLX+ System sequencer commercially available from Roche, or a MiSeq System sequencer commercially available from Illumina, Inc. may be used. In addition, the sequencer 20 may read nucleotide sequences of the 16S ribosomal RNA gene as nucleotide sequences of microorganism genes. This is because the nucleotide sequence of the 16S ribosomal RNA gene is a sequence that is relatively specific for each type of microorganism. Here, in order to read the nucleotide sequence of the 16S ribosomal RNA gene, a sequence sample (sludge sample) that is collected from activated sludge and input to the sequencer 20 is prepared in advance. The activated sludge is collected from, for example, an aerobic tank and an anaerobic tank, respectively. The preparation of a sequence sample and the reading (sequencing) of nucleotide sequences can be performed, for example, as follows.

[Preparation of Microbial Flora DNA]

About 1.5 ml of a solution containing of microorganism groups is collected from activated sludge and centrifuged at room temperature (13,000 rpm×5 minutes). The supernatant is removed, 1 ml of a sterile physiological saline is then added, mixing by inversion is performed for about 5 seconds, and then centrifugation is performed at room temperature (13,000 rpm×5 minutes). After the supernatant is removed, 300 µl of a lysis buffer (commercially available from AMR Inc.) is added and suitable mixing is performed. Then, the obtained suspension is added to a tube (Easy Extract for DNA (commercially available from AMR Inc.)) containing beads, and then stirred and disintegrated using a vortex mixer for 2 minutes. 300 µl of a TE solution (10 mM Tris, 1 mM EDTA, pH 8.0) (hereinafter referred to as TE) is added to the disintegrated solution and centrifugation is performed at 4° C. (13,000 rpm×5 minutes). Then, 450 µl of the supernatant solution is put into a new tube, and 600 µl of a phenol mixture (included in Easy Extract for DNA (commercially available from AMR Inc.)) is added thereto, stirring is performed for 1 minute using a vortex, and then centrifugation is performed at 4° C. (13,000 rpm×5 minutes). 300 µl of the supernatant is collected and put into a new tube (1.5 ml), and 1200 µl of ethanol (99.5%) is added thereto and centrifugation is performed at 4° C. (13,000 rpm×5 minutes). After the supernatant is removed, 1000 µl of cold ethanol (70%) is added and centrifugation is performed at 4° C. (13,000 rpm×5 minutes). The obtained DNA pellets are dried in a vacuum and then 150 µl of TE is added to prepare a bacterial flora DNA solution.

[PCR Amplification of V3-V4 Region of 16S Ribosomal RNA Gene]

A concentration of double-stranded DNA in the bacterial flora DNA solution is measured, 50 ng of DNA is set as a template on the basis of the measurement value, and PCR is performed to amplify the V3-V4 region of the 16S ribosomal RNA gene (hereinafter referred to as 16S gene) using a universal primer set (forward primer fw357F (SEQ ID NO. 1) and a reverse primer RV926r (SEQ ID NO. 2)). For PCR, using "Premix Ex Taq Hot Start Version" (registered trademark) commercially available from TAKARA BIO Inc., 50 µl of a reaction solution containing each of the primers at 50 pmol is prepared, and preheated at 94° C. for 2 minutes, and then denaturation at 98° C.×10 seconds, annealing at 50° C.×30 seconds, and extension at 72° C.×80 seconds are repeated over 25 cycles.

The structure of a sequence of a forward primer HA13621-fw357F is shown below. The forward primer includes the adapter A sequence (indicated by the upper case letters) necessary for sequence determination in the sequencer 20 on the 5' end side, and includes a universal primer sequence fw357F (indicated by the lower case letters) that is used to anneal all 16S genes of Eubacteria on the 3' end side with a barcode sequence of 10 nucleotides specific to each specimen therebetween. The barcode sequence is used to identify samples and is a nucleotide sequence that is arbitrarily designed to correspond to the number of samples provided to the sequencer 20.

Adapter A sequence
(SEQ ID NO. 3)
5'-CCATCTCATCCCTGCGTGTCTCCGACTCAG-3'

Universal primer sequence fw357F
(SEQ ID NO. 1)
5'-cctacgggaggcagcag-3'

The role of the barcode sequence will be described. For example, when 10 specimens are analyzed at the same time, HA13621-fw357F primers having 10 different barcode sequences may be prepared and amplified by PCR for the specimens. When these are mixed and provided to the sequencer 20, if the GS FLX+System sequencer capable of obtaining 1 million data items in one operation is used, 100 barcode sequences corresponding to 100 specimens are used. Thus, it is possible to obtain sequence data of 10,000 data/specimen items in one operation.

The structure of a sequence of a reverse primer HA13619-RV926r is shown below. The reverse primer includes the adapter B sequence (indicated by the upper case letters) necessary for sequence determination in the sequencer 20 on the 5' end side and includes a universal primer sequence RV926r (indicated by the lower case letters) that is used to anneal all 16S genes of Eubacteria on the 3' end side.

Sequence of HA13619-RV926r
(SEQ ID NO. 4)
5'-CCTATCCCCTGTGTGCCTTGGCAGTCTCAGccgtcaattcct ttttagttt-3'

According to PCR using the above universal primer set, DNA (about 570 nucleotides) including V3-V4 regions of 16S genes of various types of bacteria constituting the bacterial flora are amplified, and a mixture thereof can be obtained as PCR product DNA thereof.

[Generation of PCR Product and Preparation of Sequence Sample]

The PCR product DNA (a mixture of DNA including V3-V4 regions of 16S genes of various types of bacteria constituting the bacterial flora) obtained from the bacterial flora DNA are mixed and treated with a DNA cleaner (commercially available from Wako Pure Chemical Industries, Ltd.), and excess primers, substrate nucleotides, and the like are removed to purify the DNA. The purified DNA is eluted with 200 µl of TE and collected. Then, the collected purified DNA solution is subjected to agarose gel electrophoresis, and a DNA fragment of about 570 bp is cut out and extracted using a MinElute Gel Extraction Kit (commercially available from QIAGEN) to prepare DNA which will be provided to the sequencer 20. This is used as a sequence sample used for the following sequencing.

[Sequencing of 16S Gene and Evaluation of Accuracy of Sequence Data]

The above sequence sample is provided to the sequencer 20 which is a GS FLX+System sequencer (commercially available from Roche) and subjected to sequencing. The sequencing conditions, processes and the like comply with protocols specified by the manufacturer. Here, in the sequencer, one molecule of the PCR product DNA prepared above is fixed to one bead. Then, fine water droplets independently formed in an emulsion including water (including PCR primers, substrate nucleotides, and DNA synthetase for amplifying a sequence template DNA) and oil are captured in beads in one-to-one correspondence. With them, PCR is performed to amplify and prepare a sequence template DNA. Therefore, the beads to which the amplified template DNA is fixed are partitioned on a titer plate, and a signal of a sequence reaction at the partitioned position is then read. Thus, it is possible to determine nucleotide sequences of PCR product DNA (a mixture of DNA including V3-V4 regions of 16S genes of various types of bacteria constituting the bacterial flora) included in the above sequence sample at random. In addition, when the above barcode sequence in the forward primer HA13621-fw357F is set as any sequence specific to each specimen derived from the samples, it is possible to analyze bacterial flora samples of about 100 types at the same time using the GS FLX+System sequencer, and it is possible to determine sequence data of 16S genes at 2,000 to 10,000 per sample derived from a certain activated sludge within about 10 to 23 hours. That is, it is possible to comprehensively analyze bacterial flora included in activated sludge without limitation to the type of bacteria.

The above is an example of a method of preparing a sequence sample and reading nucleotide sequences. Here, the preparation of a sequence sample and the reading of nucleotide sequences may be performed by a method other than the above method. The sequencer 20 and the computer 10 are connected so that information is transmitted and received therebetween. The sequencer 20 transmits information indicating the read a nucleotide sequence for each microorganism (sequence information) to the computer 10.

Here, the sequence information transmitted to the computer is sequence data without change sequenced in the sequencer 20 which is so-called rough sequence data.

Subsequently, functions of the computer 10 according to the present embodiment will be described. As shown in FIG. 1, the computer 10 includes a data generating unit 11, an input unit 12, a principal component analyzing unit 13, a prediction rule generating unit 14, and a prediction unit 15.

The data generating unit 11 is data generating means configured to receive nucleotide sequences of a plurality of microorganisms included in activated sludge which are read by the sequencer 20 from the sequencer 20 and generate data for generating a prediction rule based on the nucleotide sequences. The data for generating a prediction rule is time series data of an abundance proportion (presence probability) of each of a plurality of microorganisms included in activated sludge. The abundance proportion is a proportion of the number of microorganisms of a type included in activated sludge for each type of microorganism (microorganism type and bacterial type) with respect to the number of all microorganisms included in the activated sludge. However, when it is difficult to strictly determine the proportion or the like, it is not necessary for the proportion to be strictly a proportion of the number thereof with respect to the number of all microorganisms, and it may be a proportion that is approximate enough to generate a prediction rule. In addition, the data indicates abundance proportions at a plurality of timings (times) for the same activated sludge (prediction target activated sludge), that is, time series data. The time series data here may be data acquired at a plurality of timings during a certain period of time, and the interval between measurement times may be constant or not constant. In order to increase prediction accuracy, the data may be acquired at substantially constant time intervals, and for example, may be data of weekly abundance proportions over a plurality of weeks. That is, a solution containing microorganism groups is collected from activated sludge every week and the abundance proportion is calculated. Therefore, the data can be, for example, matrix data of the number of types of microorganism×the number of timings of a time series.

In addition, when an activated sludge layer is divided into an aerobic tank and an anaerobic tank, data items of abundance proportions in each of the aerobic tank and the anaerobic tank may be obtained and set as other time series data items, and both may be used for the subsequent processing. The type of microorganism is not limited to a specific type of microorganism involved in decomposition of a treatment target substance in water to be treated, and it may be any type to be analyzed at random. The number of types of microorganism depends on the activated sludge, and is a number of about 20,000. Among all types of microorganism appropriately obtained, those having a high abundance proportion may be selected, and data about microorganism types that make up 50% or more of the total number of microorganism types may be used, and further 75% or more may be used. Appropriately obtained microorganism types, for example, as will be described below, are types other than types having a very small number of sequence data items (a count of the number of sequences) (for example, 1, 2, or 3) among all OTU types obtained by OTU analysis. When the number of microorganism types is selected, abundance proportions of microorganism types in each data at each time constituting time series data of microorganism information are calculated, the sum of abundance proportions for all the times for each microorganism type is set as an abundance proportion of each microorganism type, and selection is performed from those having a high abundance proportion. In addition, the number of timings may correspond to, for example, data for half a year. That is, the number of timings is about several tens to several hundreds. In the above data generation and the following data processing, instead of the abundance proportion of microorganisms, an abundance proportion of each of a plurality of nucleotide sequences included in activated sludge can be used, or both the abundance proportion of microorganisms and the abundance proportion of nucleotide sequences can be used.

For example, the data generating unit 11 generates the data as follows. The data generating unit 11 receives rough sequence data from the sequencer 20. Here, the rough sequence data received from the sequencer 20 is data about activated sludge at a plurality of timings, and is a number of data items at which an abundance proportions of each of a plurality of microorganisms or nucleotide sequences included in activated sludge at each timing can be predicted. That is, sequencing is performed by the sequencer 20 such that such data is obtained. The plurality of timings correspond to respective timings of time series data.

Regarding the obtained rough sequence data (for example, about 570 nucleotides/data in the above example), the data generating unit 11 allocates each sequence to each of specific samples (corresponding to each timing of time series data) based on barcode sequences specific to samples included in sequence data. The data generating unit 11 removes sequence data having a sequence length of less than 200 and 1000 or more, sequence data having one or more mismatches with the universal primer sequence (fw357F), and sequence data having an average quality value (25 or less) of nucleotide sequences whose sequences are determined using a quality program provided to the sequencer, and extracts high accuracy data.

The data generating unit 11 provides the acquired high accuracy sequence data for operational taxonomic unit analysis (hereinafter referred to as OTU analysis) according to clustering (a threshold value of 95%, 97%, or 99% in similarity). In the OTU analysis, an operation of grouping sequence data items based on the similarity of sequence data is performed. Here, a cluster group (hereinafter referred to as OTU) of sequence data having a sequence similarity of 95% or more is detected. Here, clustering of sequence data can be performed using a technique in the related art, for example, the freeware Uclust. OTUs can be inferred to be derived from almost the same type of bacteria (microorganism). Thus, the total number of OTUs (OTU number) obtained according to clustering is considered to be equivalent to the number of bacterial types (microorganism types) constituting the bacterial flora (microbial flora) within a detectable range. The data generating unit 11 determines representative sequence data which is nucleotide sequences representing each cluster group. Determination of representative sequence data can be performed by a method used conventionally.

In addition, the proportion of each OTU in the total number of sequence data items, that is, a bacterial type composition proportion or a nucleotide sequence composition proportion, in other words, the above abundance proportion, can be obtained from the number of sequence data items included in each OTU. Furthermore, when a homology search for representative sequence data of each OTU is performed on the above 16S gene and a bacterial genome database, it is possible to identify belonging to known bacterial types having the highest sequence similarity, that is, a bacterial type of OTU. Here, in the present embodiment, identification of bacterial types is not necessarily required. However, since then it is possible to determine specifically which types of bacteria are included in activated sludge, it is beneficial in analysis of the prediction result or the like. Here, since an OTU (cluster group) in which the number of sequence data items (a count of the number of sequences) included in data at all times constituting time series data of microorganism information is very small (for example, 1, 2 or 3) is not beneficial information in many nucleotides, and serves as noise during computation, it may be excluded from time series data in advance.

The data generating unit 11 calculates abundance proportions for each type of bacteria or each type of nucleotide sequence at a plurality of timings, and thus generates time series data, for example, in the format of the above matrix. The data generating unit 11 outputs the generated time series data to the input unit 12.

The input unit 12 is input means configured to input time the above series data of the microorganism information and water quality information indicating water quality after a water treatment associated with data at each time constituting the time series data. The input unit 12 inputs the above time series data of the microorganism information from the data generating unit 11. The water quality information indicates a state of water quality at a timing, and indicates, for example, whether water quality data such as BOD will exceed a preset threshold value within a preset period (for example, one week) from the above timing (a timing at which a solution containing microbial flora is collected from activated sludge) in time series data. The threshold value is similar to a threshold value according to the above prediction rule. The water quality information can be obtained by measuring water quality data such as BOD in water after a water treatment. While it is desirable that water quality data such as BOD be measured with a high frequency, for example, every day, measurement may be performed according to the above period. For example, when the water quality information indicates whether water quality data such as BOD will exceed a preset threshold value within one week, measurement may be performed about twice over one week. For example, when water quality data such as BOD will exceed a preset threshold value within one week, the water quality information may be set to 1, and otherwise, 0.

For example, when the computer 10 receives an input operation of water quality information from a user, the water quality information is input. The water quality information may be information for each data item at the above timing in time series data of microorganism information, and may include information about the timing number in the time series. The input unit 12 inputs water quality information associated with each data item at each timing. For example, water quality information input to the computer 10 may be associated with information indicating a timing of water quality information. Here, the input unit 12 may input values of water quality data such as BOD in time series, determine whether the value will exceed a threshold value within one week from the above timing, and generate the above water quality information. The timings of water quality data such as BOD in a time series may not be the same as the timing of time series data of microorganism information.

Within information input by the input unit 12, time series data of microorganism information corresponds to data input to a prediction rule generated by the prediction-rule generating system 1. In addition, water quality information corresponds to water quality predicted by the prediction rule generated by the prediction-rule generating system 1. The input unit 12 outputs time series data of microorganism information within input information to the principal component analyzing unit 13. The input unit 12 outputs water quality information within input information to the prediction rule generating unit 14.

The principal component analyzing unit 13 is principal component analyzing means configured to perform principal component analysis on time series data of microorganism information input by the input unit 12 and calculate principal component scores of data at each time constituting the time series data. As described above, since time series data is matrix data, it is possible to perform principal component analysis. The principal component analyzing unit 13 calculates principal component scores of data at each time constituting time series data, that is, data of abundance proportions of microorganisms or nucleotide sequences included in activated sludge at each timing. That is, principal component analysis is performed to reduce the number of types of microorganism of matrix data or nucleotide sequences (variables). When time series data of microorganism information is acquired from the aerobic tank and the anaerobic tank, principal component analysis is performed on a combination of both data items. In this case, principal component scores is calculated for time series data of microorganism information of each of the aerobic tank and the anaerobic tank.

Specifically, the principal component analyzing unit 13 may perform principal component analysis using a correlation matrix in consideration of characteristics of microorganisms included in activated sludge for a water treatment. That is, time series data of microorganism information is converted into a correlation matrix and principal component analysis is then performed. By performing principal component analysis using a correlation matrix, it is possible to reflect behaviors of microorganisms of minority species. However, a variance-covariance matrix can be used according to a composition of microorganisms included in activated sludge. The principal component analysis can be performed using software packages of the related art.

For example, regarding data at each time constituting time series data of microorganism information, the principal component analyzing unit 13 may set principal component scores as principal component scores used in the following process until a cumulative contribution proportion is a preset threshold value (for example, 80%) or higher. In addition, the principal component analyzing unit 13 may use a preset number of principal component scores in descending order of contribution proportions as principal component scores used in the following process. Alternatively, any other type of principal component score may be used as a principal component score used in the following process. The number of principal component scores used in the following process can be approximately ten to several tens (for each data item at each time constituting time series data) in consideration of a processing load in the following process. As will be described below, in order to select a principal component score used in the prediction unit, a large number of principal component scores are calculated here. The principal component analyzing unit 13 outputs the calculated principal component scores of data at each time constituting time series data as principal component scores used in the following process to the prediction rule generating unit 14. In addition, in order to perform prediction according to the prediction rule, the principal component analyzing unit 13 stores information for calculating principal component scores from vector data of abundance proportions of microorganisms or nucleotide sequences. Alternatively, time series data of microorganism information used for the prediction rule and microorganism information used for prediction are simultaneously generated by the data generating unit 11, and input by the input unit 12. Both data items are combined as matrix data, and principal component scores used for the prediction rule and principal component scores used for prediction can be computed in advance at the same time.

Figure 2:
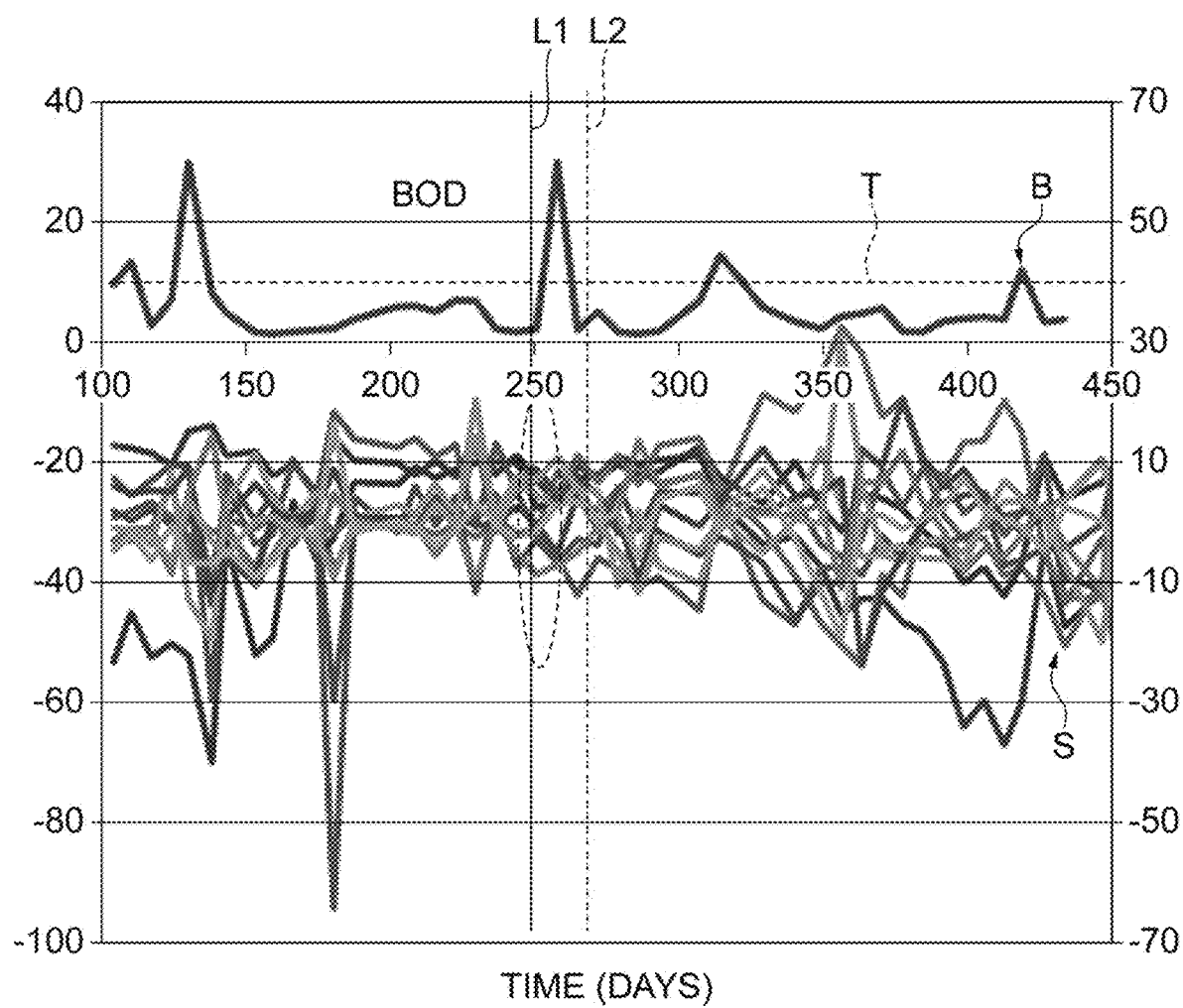
FIG. 2 is a graph of examples of time series data of principal component scores (12 among all principal component scores are shown) of an abundance proportion of each of a plurality of microorganisms included in activated sludge and BOD.

The prediction rule generating unit 14 is prediction rule generating means configured to generate a prediction rule for predicting water quality after a water treatment from an abundance proportion of each of a plurality of microorganisms or nucleotide sequences on the basis of the principal component scores of data at each time constituting time series data of microorganism information calculated by the principal component analyzing unit 13 and water quality information associated with data at each time constituting the time series data input by the input unit 12. FIG. 2 is a graph of examples of time series data of principal component scores and BOD serving as the source of water quality information. In the graph in FIG. 2, the horizontal axis represents a time, and the vertical axis represents the value of the principal component score and the value of BOD. As the principal component score, principal component scores of the first to sixth contribution proportions when principal component analysis using a correlation matrix is performed are shown. A total of 12 including six principal component scores of the aerobic tank and six principal component scores of the anaerobic tank are shown. As the principal component scores used for the prediction rule, 10 principal component scores are selected from 30 principal component scores of each of the aerobic tank and the anaerobic tank. Each of a plurality of lines S indicates the value of the principal component score. In addition, a line B indicates the value of BOD.

The prediction rule is used to predict, from a principal component score at a certain timing (a timing at which microbial flora are observed, for example, a timing indicated by a solid line L1 in FIG. 2), a state of water quality at that timing and a timing thereafter, and is used to, for example, predict whether BOD will exceed a preset threshold value T within a preset period (for example, a period to the timing indicated by a dashed line L2 in FIG. 2) from the timing.

Specifically, the prediction rule generating unit 14 generates a prediction rule by performing, for example, machine learning (training by machine learning) on the basis of the principal component score of data at each time constituting input time series data of microorganism information and water quality information associated with data at each time constituting the time series data. That is, the principal component score of data at each time constituting the input time series data and water quality information associated with data at each time constituting the time series data are correct answer data (sample data) for machine learning. In the machine learning, the principal component score of data at each time constituting time series data of microorganism information is used as an input (explanatory variable) for the prediction rule and water quality information indicating water quality after a water treatment associated with data at each time constituting the time series data is used as an output (objective variable) in the prediction rule. Furthermore, a principal component score used as an explanatory variable may be selected here. A larger number of principal component scores used for prediction does not necessarily serve higher prediction accuracy, and a higher contribution proportion of the principal component score does not necessarily serve higher prediction accuracy. Machine learning is performed by variously changing combinations of principal component scores calculated by the principal component analyzing unit, prediction accuracy thereof is repeatedly evaluated, and a combination of principal component scores whose prediction accuracy is a certain reference value or higher is selected as an explanatory variable. The reference value can be, for example, 75% or 85%.

As methods of machine learning, for example, linear regression models can be used. A Bayesian estimation method may be used in this case. In addition, a binomial or ordered discrete selection model can be used as one of the linear regression models. Specifically, a probit model, a logit model, or a tobit model can be used. The Bayesian estimation method can be used for this model or a support vector machine (SVM) or the like can be used. Alternatively, a Bayesian network may be used. The prediction rule generating unit 14 outputs information indicating the generated prediction rule to the prediction unit 15.

The prediction unit 15 is predicting means configured to predict water quality after a water treatment based on the prediction rule generated by the prediction rule generating unit 14. As described above, the prediction rule is used to predict a state of water quality data such as BOD at a prediction time and thereafter on the basis of the principal component score, and is used to predict, for example, whether water quality data such as BOD will exceed a preset threshold value within a preset period from the prediction time. That is, the prediction unit 15 inputs principal component scores related to a prediction target and performs prediction on the basis of the prediction rule. The prediction target is (microbial flora of) a water treatment system in which activated sludge including microbial flora (at a timing at which prediction is desired to be performed) is used. The prediction target water treatment system can be the same as a water treatment system that has acquired data used for generating the prediction rule. However, the prediction target water treatment system may be a system other than the water treatment system that has acquired data used for generating the prediction rule.

The prediction target principal component scores are obtained in the same manner as in the principal component scores related to one timing of time series data of microorganism information when the prediction rule is generated. That is, the principal component scores are generated as follows. The sequencer 20 reads nucleotide sequences of genes from a plurality of microorganisms included in activated sludge of the prediction target water treatment system. The sequencer 20 transmits information (sequence information) indicating the read a nucleotide sequence for each of the plurality of prediction target microorganisms to the computer 10.

In the computer 10, the data generating unit 11 receives sequence information from the sequencer 20, and generates data of an abundance proportion of each of a plurality of microorganisms or nucleotide sequences serving as a prediction target from the sequence information. The data can be, for example, vector data including elements of the number of types of microorganism or nucleotide sequences. Here, the vector data corresponds to matrix data for generating a prediction rule. That is, the order of the value of the abundance proportions for each type of microorganisms or nucleotide sequences, and the number of types of microorganisms or nucleotide sequences (the number of elements of vector data) are the same in matrix data for generating a prediction rule and vector data for prediction.

The data generating unit 11 outputs the generated vector data for prediction related to abundance proportions of microorganisms or nucleotide sequences to the input unit 12. The input unit 12 inputs the vector data and outputs the input data to the principal component analyzing unit 13. The principal component analyzing unit 13 inputs the vector data, and calculates principal component scores of the vector data based on principal component analysis performed when a prediction rule is generated. The principal component analyzing unit 13 outputs the calculated principal component scores to the prediction unit 15. In addition, the prediction target principal component scores is obtained at the same time as when principal component scores of time series data of microorganism information when a prediction rule is generated is obtained. That is, the prediction target principal component scores is calculated by increasing the number of timings of matrix data (the number of microorganism types×timings) for generating a prediction rule and incorporating vector data for prediction.

The prediction unit 15 inputs the prediction target principal component scores input from the principal component analyzing unit 13 to a prediction rule and obtains an output from the prediction rule as a prediction result. The prediction result corresponds to the generated prediction rule, and is information indicating whether water quality data such as BOD will exceed a preset threshold value within a preset period (for example, one week) from a prediction time in the example shown in the present embodiment. The prediction unit 15 outputs the obtained prediction result. The output of the prediction result is performed by, for example, displaying the prediction result on a display device such as a display included in the computer 10. In addition, the output of the prediction result may be performed by, for example, transmitting the prediction result to another device or another module in the computer 10. Functions of the computer 10 according to the present embodiment are as described above.

Figure 3:
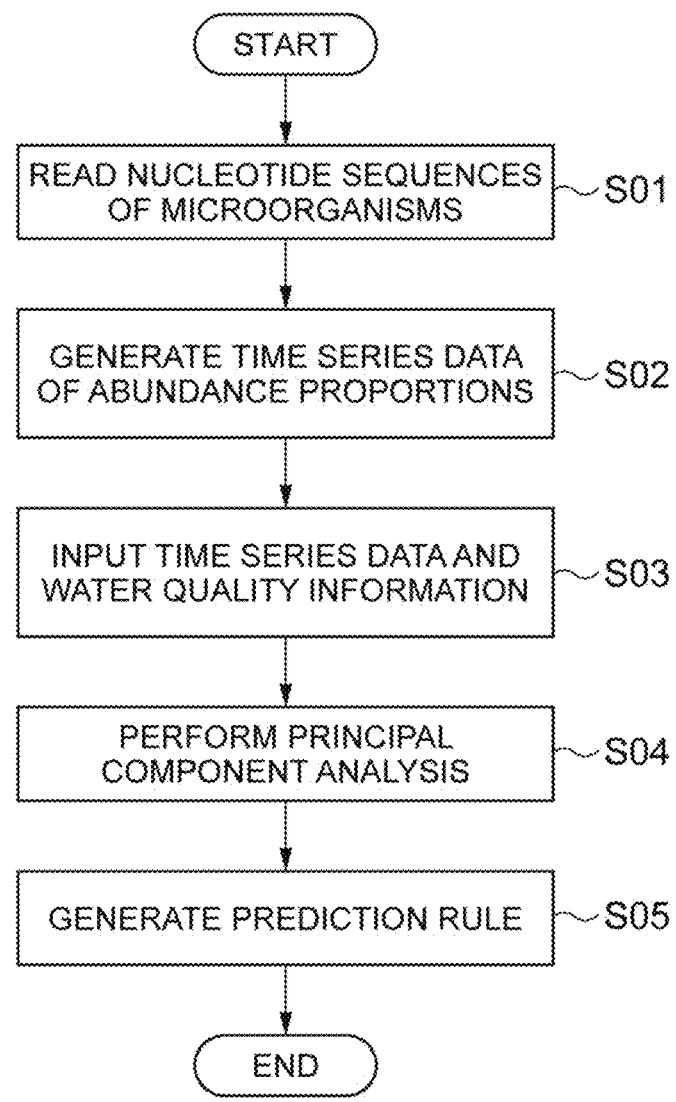
FIG. 3 is a flowchart showing processes (prediction-rule generating method) preformed when the prediction-rule generating system according to the embodiment of the present invention generates a prediction rule.
Figure 4:
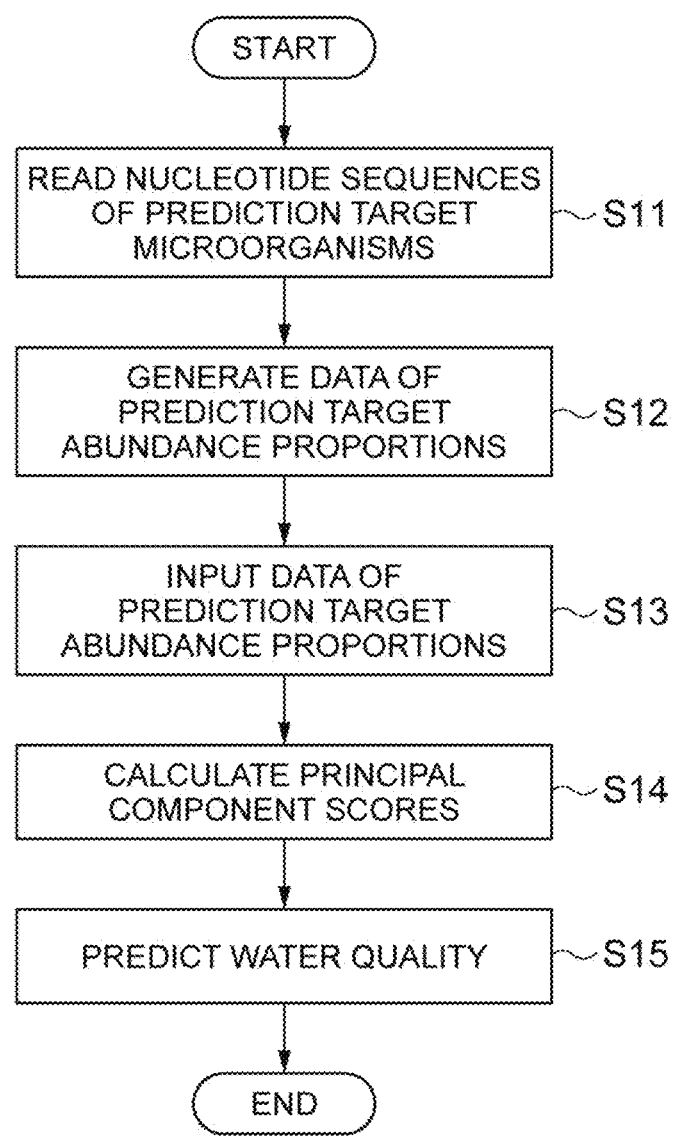
FIG. 4 is a flowchart showing processes (prediction method) performed when the prediction-rule generating system according to the embodiment of the present invention performs prediction.

Subsequently, a prediction-rule generating method and a prediction method which include processes (method of operating the prediction-rule generating system 1) performed by the prediction-rule generating system 1 according to the present embodiment will be described with reference to flowcharts in FIG. 3 and FIG. 4. First, a process performed when a prediction rule is generated will be described with reference to the flowchart in FIG. 3. In this process, first, the sequencer 20 reads nucleotide sequences of genes of microorganisms constituting microbial flora using a water treatment system (S01, reading step). Here, nucleotide sequences of genes of microorganisms constituting microbial flora are read at a plurality of timings. The read nucleotide sequence data is output from the sequencer 20 to the computer 10.

In the computer 10, the data generating unit 11 receives the nucleotide sequence data transmitted from the sequencer 20. Next, the data generating unit 11 generates time series data of microorganism information based on the nucleotide sequence data (S02, data generating step). As described above, the generated time series data is matrix data of the number of types of microorganisms or nucleotide sequences×the number of timings in a time series. Next, the generated time series data is input to the input unit 12 from the data generating unit 11. In addition, the input unit 12 inputs water quality information for each data item at the above timing along with the input of time series data (S03, input step). The input of water quality information is performed by, for example, reading a data file that is regularly or irregularly updated or accepting an input operation of water quality information to the computer 10 from a user.

The input time series data of microorganism information is output from the input unit 12 to the principal component analyzing unit 13. In addition, the input water quality information is output to the prediction rule generating unit 14 from the input unit 12. Next, the principal component analyzing unit 13 performs principal component analysis on time series data of microorganism information (S04, principal component analyzing step). The principal component scores of data at each time constituting time series data obtained through principal component analysis is output to the prediction rule generating unit 14 from the principal component analyzing unit 13.

Next, the prediction rule generating unit 14 generates a prediction rule on the basis of the principal component scores input from the principal component analyzing unit 13 and water quality information associated with data at each time constituting the time series data input from the input unit 12 (S05, prediction rule generating step). As described above, the prediction rule is generated by, for example, machine learning in which principal component scores is used as an input (explanatory variable) for the prediction rule and water quality information is used as an output (objective variable) for the prediction rule. Information indicating the generated prediction rule is output to the prediction unit 15 from the prediction rule generating unit 14. The process performed when a prediction rule is generated is as described above.

Subsequently, a process performed when prediction is performed will be described with reference to the flowchart in FIG. 4. In this process, first, the sequencer 20 reads nucleotide sequences of genes of microorganisms constituting microbial flora used in the water treatment system at a prediction target timing (S11, reading step). The read nucleotide sequence data is output to the computer 10 from the sequencer 20.

In the computer 10, the data generating unit 11 receives the nucleotide sequence data transmitted from the sequencer 20. Next, the data generating unit 11 generates data of an abundance proportion of each of microorganisms or nucleotide sequences based on nucleotide sequence data (S12, data generating step). As described above, the generated data is vector data including elements of the number of types of microorganisms or nucleotide sequences. Next, the generated data is input to the input unit 12 from the data generating unit 11 (S13, input step).

The input data is output to the principal component analyzing unit 13 from the input unit 12. Next, the principal component analyzing unit 13 calculates principal component scores of the input data based on the principal component analysis performed when a prediction rule is generated (S14, principal component analyzing step). The principal component scores of data obtained through the principal component analysis is output to the prediction unit 15 from the principal component analyzing unit 13.

Next, the prediction unit 15 predicts water quality from the principal component scores input from the principal component analyzing unit 13 based on the prediction rule generated by the prediction rule generating unit 14 (S15, predicting step). For example, information indicating the prediction result is displayed so that a user can recognize the result. The process performed when prediction is performed is as described above.

As described above, according to the present embodiment, the prediction rule is generated on the basis of time series data of microorganism information and water quality information indicating water quality after a water treatment associated with data at each time constituting the time series data. Therefore, prediction can be performed in consideration of states of microbial flora in activated sludge unlike prediction using only time series data of water quality and operating parameters of the biological reaction tank. Thus, prediction is performed accurately compared to when prediction is performed using only time series data of water quality and operating parameters of the biological reaction tank.

In addition, according to the present embodiment, principal component analysis is performed. In general, the number of types of microorganism included in activated sludge is extremely large. By performing principal component analysis on time series data of microorganism information, all information is captured without reducing an amount of information, and it is possible to express microorganism information with a small number of variables. By performing principal component analysis as in the present embodiment and reducing the number of variables used to generate a prediction rule, the prediction rule can be reliably generated. That is, according to the present embodiment, it is possible to generate a prediction rule by which water quality after a water treatment is predicted accurately and reliably.

As in the present embodiment, in principal component analysis, a correlation matrix may be used. By performing principal component analysis using a correlation matrix, compared to when a variance-covariance matrix is used, it is possible to generate a prediction rule in which behaviors of microorganisms of minority species (microorganisms having a small abundance proportion) are better reflected even if principal component analysis is performed. Behaviors of microorganisms of minority species may influence water quality after a water treatment. Therefore, in such a configuration, it is possible to generate a prediction rule by which prediction is performed more accurately. However, as described above, depending on the composition of microorganisms included in activated sludge or the like, a variance-covariance matrix may be used.

In addition, as in the present embodiment, a prediction rule may be generated by machine learning. In such a configuration, it is possible to reliably generate a prediction rule. However, machine learning is not necessarily used always, and a prediction rule may be generated by other methods. For example, a prediction rule may be generated using time series analysis. Specifically, time series analysis such as a multivariable autoregressive (VAR) model may be used.

In addition, as in the present embodiment, the sequencer 20 configured to read nucleotide sequences of microorganism genes may be included in the prediction-rule generating system 1, and time series data may be generated based on the read nucleotide sequences. In such a configuration, it is possible to reliably input time series data of abundance proportions of microorganisms or nucleotide sequences, and it is possible to reliably implement an embodiment of the present invention. However, the prediction-rule generating system 1 does not necessarily always include the sequencer 20. That is, (the input unit 12 of the computer 10 of) the prediction-rule generating system 1 may input time series data of microorganism information from the outside.

In addition, a component configured to perform prediction using the prediction rule generated according to the present embodiment may be included. That is, the prediction-rule generating system 1 may also serve as a prediction system as in the present embodiment. In such a configuration, it is possible to perform prediction based on the generated prediction rule. However, prediction is not necessarily always performed by the prediction-rule generating system 1, and may be performed by a device or a system other than the prediction-rule generating system 1. In this case, the prediction rule generated by the prediction-rule generating system 1 is output to a prediction system other than the prediction-rule generating system 1. The prediction system has a function of prediction performed by the prediction-rule generating system 1 described above.

Figure 5:
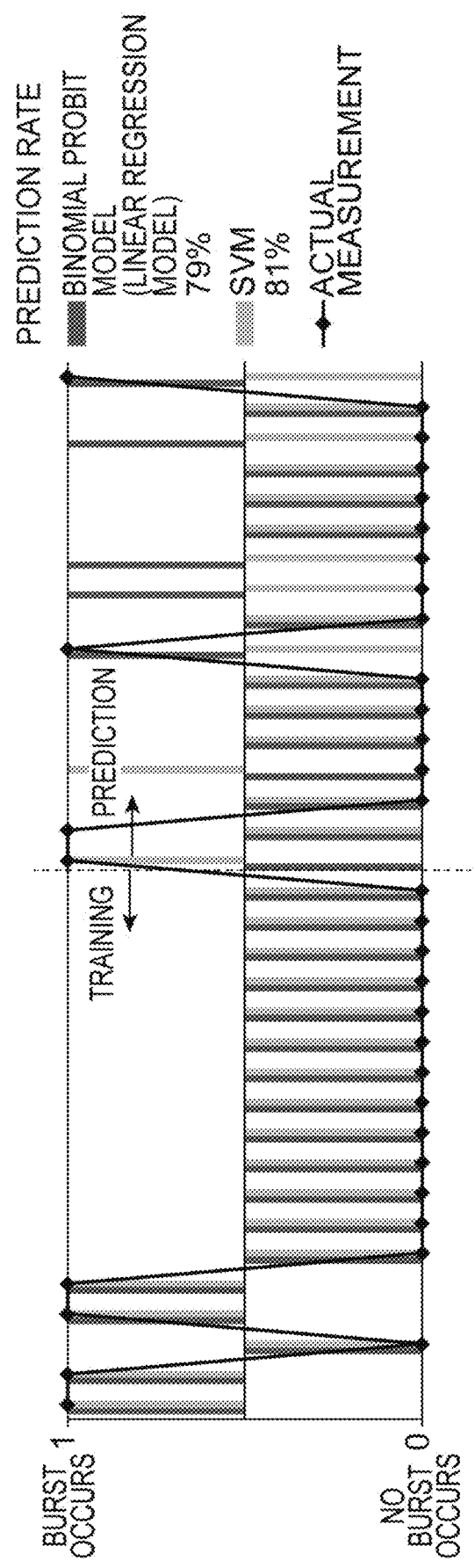
FIG. 5 is a graph showing an example of prediction results obtained by using the generated prediction rule.

Next, examples of prediction results using the prediction rule generated by the prediction-rule generating system 1 of the present embodiment will be described. FIG. 5 shows the graph of examples of the prediction results. In FIG. 5, the horizontal axis represents the time axis. One point in the horizontal axis corresponds to one of timings described above. The vertical axis indicates whether BOD exceeds a preset threshold value within one week from the timing (prediction time), that is, whether a burst occurs (BOD exceeds a threshold value within one week) or does not occur (BOD does not exceed a threshold value within one week). In this example, results obtained when a binomial probit model (linear regression model) according to the Bayesian estimation method is used or SVM is used as a method of machine learning when a prediction rule is generated are shown. In FIG. 5, data on the left side of the dashed line is used for training of machine learning, and data on the right side of the dashed line is not used for training of machine learning. The values obtained when the probit model is used or when the SVM is used are prediction results (output from the prediction rule) using the prediction rule.

As shown in FIG. 5, when the probit model is used as a method of machine learning, the output of data that is not used for training of machine learning is a 79% match with actual measurement. When the SVM is used as a method of machine learning, the output of data that is not used for training of machine learning is an 81% match with actual measurement. That is, a prediction rate with the method of the present embodiment is approximately 80%, which is a high value. In the example shown in FIG. 5, a prediction model (prediction rule) generated using half year training data (data on the left side of the dashed line) is used to predict a value of BOD to which the prediction rule is applied for the second half year. Specifically, it is predicted whether BOD will exceed a threshold value at each timing of time series data of abundance proportions of microorganisms for the second half year. When a prediction rule that is updated and generated based on data acquired more recently (for example, 1 to 2 weeks ago) is used, the prediction rate is considered to be higher. In daily water quality management, prediction may be performed while the prediction rule is updated by adding newly acquired data.

Subsequently, modified examples of the above embodiment will be described. In the above embodiment, as an input for the prediction rule, data of abundance proportions of microorganisms or nucleotide sequences is used. In addition thereto, other data may be used as an input. As the other data, for example, water quality data of treated water (wastewater) and operating parameters of the biological reaction tank which are used to predict water quality in the related art may be used. Specifically, water quality data such as chemical oxygen demand (COD), a temperature, TOC and TN, pH, wastewater items, an amount of dissolved oxygen (DO), and operating parameters of the biological reaction tank such as an oxidation-reduction potential (ORP) may be used. Alternatively, data about conditions of water to be treated flowing into the water treatment system may be used. In addition, in the wastewater treatment system in which wastewater items are switched and used, wastewater items treated at that time or immediately thereafter can be used for data. When data other than the data of abundance proportions of microorganisms or nucleotide sequences is used, correct answer data for these data items may be prepared and machine learning may be performed. These data items are combined and a combination of data items with high prediction accuracy can be selected. When the number of data items serving as the source for prediction increases, it is possible to generate a prediction rule with higher accuracy. When data items that can be acquired highly frequently are combined, it is possible to perform finer water quality management (prediction).

In the above embodiment, water quality to be predicted is whether BOD will exceed a preset threshold value within a preset period from a prediction time. However, the prediction rule generated in the present invention may be used to predict other indexes as long as they are related to water quality. For example, prediction of water quality such as COD, TOC, and TN may be exemplified. Not only determination of whether a value of water quality will exceed a threshold value but also prediction of a level in which a value is included among a plurality of levels divided according to a certain range or prediction of an approximate estimated value may be performed.

REFERENCE SIGNS LIST

1 Prediction-rule generating system
10 Computer
11 Data generating unit
12 Input unit
13 Principal component analyzing unit
14 Prediction rule generating unit
15 Prediction unit
20 Sequencer

The invention claimed is:

1. A system for monitoring a water quality of water treatment using microorganisms, the system comprising at least one processor configured to:
receive time series data comprising, for each time point of a plurality of time points, a data item comprising
at least one of an abundance proportion of each microorganism of a plurality of types microorganisms included in an activated sludge in a biological reaction tank or an abundance proportion of each of a plurality of nucleotide sequences obtained from the plurality of types microorganisms, and
a water quality information comprising values of at least one parameter related to quality of water after a water treatment using the activated sludge;
iteratively perform a principal component analysis by applying a machine learning technique to the time series data to calculate principal component scores, each score being associated with a time point of the plurality of time points;
generate at least one prediction rule based on the calculated principal component scores;
receive a prediction target data comprising at least one of an abundance proportion of each microorganism in a plurality of target types microorganisms included in a target activated sludge or an abundance proportion of each of a plurality of nucleotide sequences obtained from the plurality of target types microorganisms;
calculate prediction target principal component scores from the prediction target data;
apply the prediction rule to the prediction target principal component scores to generate a prediction result regarding a quality of water after a water treatment using the target activated sludge, the prediction result comprising a predicted value of the at least one parameter;
display a graphical representation of the prediction result on a display of a computing device, wherein the representation indicates whether the predicted value of the at least one parameter is different than a threshold value within at least one time period from a prediction time, and
generate an instruction, based on the predicted value of the at least one parameter, regarding whether or not to discharge the water into a natural environment after the water treatment.

2. The system of claim 1, wherein the time series data is acquired at the plurality of time points that are substantially constant time intervals.

3. The system of claim 1, wherein the biological reaction tank comprises at least one of an aerobic tank and an anaerobic tank.

4. The system of claim 1, wherein the system further comprises a sequencer, and wherein the time series data is received from the sequencer.

5. The system of claim 1, wherein the at least one parameter of the water quality information related to water quality comprises one or more of a temperature, pH, biochemical oxygen demand (BOD), chemical oxygen demand (COD), total organic carbon (TOC), an amount of dissolved oxygen (DO), and total nitrogen (TN).

6. The system of claim 1, wherein the time series data further comprises at least one operating parameter of the biological reaction tank.

7. The system of claim 1, wherein the water quality information comprises an indication of whether a value of the at least one parameter exceeds a threshold.

8. The system of claim 1, wherein the principal component analysis is performed on the time series data in the form of a correlation matrix.

9. The system of claim 1, wherein the at least one processor:
performs the principal component analysis by calculating a plurality of principal component scores comprising a principal component score for each data item in the time series data; and
selects principal component scores from the plurality of principal component scores for generation of the prediction rule thereby reducing a number of types of microorganism from the plurality of types microorganisms or reducing a number of nucleotide sequences from the plurality of nucleotide sequences that are used for generation of the prediction rule.

10. The system of claim 1, wherein the machine learning technique comprises support vector machine (SVM), linear regression, or a Bayesian classifier.

11. The system of claim 1, wherein the target activated sludge is the same as the activated sludge for which the time series data is generated.

12. The system of claim 1, wherein the graphical representation of the prediction result indicates whether the predicted value of the at least one parameter exceeds the threshold value within the at least one time period from the prediction time.

13. The method of claim 1, wherein the graphical representation of the prediction result indicates whether the predicted value of the at least one parameter exceeds the threshold value within the at least one time period from the prediction time.

14. A method for monitoring a water quality of water treatment using microorganisms, comprising operating at least one processor to:
receive time series data comprising, for each time point of a plurality of time points, a data item comprising
at least one of an abundance proportion of each microorganism of a plurality of types microorganisms included in an activated sludge in a biological reaction tank or an abundance proportion of each of a plurality of nucleotide sequences obtained from the plurality of types microorganisms, and
a water quality information comprising values of at least one parameter related to quality of water after a water treatment using the activated sludge;
iteratively perform a principal component analysis by applying a machine learning technique to the time series data to calculate principal component scores, each score being associated with a time point of the plurality of time points;
generate at least one prediction rule based on the calculated principal component scores;
receive a prediction target data comprising at least one of an abundance proportion of each microorganism in a plurality of target types microorganisms included in a target activated sludge or an abundance proportion of each of a plurality of nucleotide sequences obtained from the plurality of target types microorganisms;
calculate prediction target principal component scores from the prediction target data;
apply the prediction rule to the prediction target principal component scores to generate a prediction result regarding a quality of water after a water treatment using the target activated sludge, the prediction result comprising a predicted value of the at least one parameter;

display a graphical representation of the prediction result on a display of a computing device, wherein the representation indicates whether the predicted value of the at least one parameter is different than a threshold value within at least one time period from a prediction time, and generate an instruction, based on the predicted value of the at least one parameter, regarding whether or not to discharge the water into a natural environment after the water treatment.

15. The method of claim 14, further comprising transmitting the prediction result to a remote device via a network.

16. The method of claim 14, wherein the at least one time period from the prediction time corresponds to time points for future analysis of water treated with the target activated sludge.

17. The method of claim 14, wherein iteratively performing the principal component analysis comprises applying the machine learning technique to both the time series data and the prediction target data, to simultaneously calculate the principal component scores and the prediction target principal component scores.

18. The method of claim 14, further comprising operating the at least one processor to:

perform the principal component analysis by calculating a plurality of principal component scores comprising a principal component score for each data item in the time series data; and select principal component scores from the plurality of principal component scores for generation of the prediction rule thereby reducing a number of types of microorganism from the plurality of types microorganisms or reducing a number of nucleotide sequences from the plurality of nucleotide sequences that are used for generation of the prediction rule.

19. The method of claim 14, wherein the machine learning technique comprises support vector machine (SVM), linear regression, or a Bayesian classifier.

20. The method of claim 14, wherein the principal component analysis is performed on the time series data in the form of a correlation matrix.

* * * * *

SEQUENCE LISTING

```
<160> NUMBER OF SEQ ID NOS: 4

<210> SEQ ID NO 1
<211> LENGTH: 17
<212> TYPE: DNA
<213> ORGANISM: Artificial
<220> FEATURE:
<223> OTHER INFORMATION: universal primer fw357F

<400> SEQUENCE: 1
cctacgggag gcagcag                                                    17

<210> SEQ ID NO 2
<211> LENGTH: 21
<212> TYPE: DNA
<213> ORGANISM: Artificial
<220> FEATURE:
<223> OTHER INFORMATION: universal primer RV926r

<400> SEQUENCE: 2
ccgtcaattc cttttragtt t                                               21

<210> SEQ ID NO 3
<211> LENGTH: 30
<212> TYPE: DNA
<213> ORGANISM: Artificial
<220> FEATURE:
<223> OTHER INFORMATION: adapter A

<400> SEQUENCE: 3
ccatctcatc cctgcgtgtc tccgactcag                                      30

<210> SEQ ID NO 4
<211> LENGTH: 51
<212> TYPE: DNA
<213> ORGANISM: Artificial
<220> FEATURE:
<223> OTHER INFORMATION: reverse primer HA13619-RV926r

<400> SEQUENCE: 4
cctatcccct gtgtgccttg gcagtctcag ccgtcaattc cttttragtt t              51
```